(12) United States Patent
Van Berkel et al.

(10) Patent No.: US 9,395,278 B2
(45) Date of Patent: Jul. 19, 2016

(54) SURFACE SAMPLING CONCENTRATION AND REACTION PROBE WITH CONTROLLER TO ADJUST SAMPLING POSITION

(71) Applicant: UT-Battelle, LLC, Oak Ridge, TN (US)

(72) Inventors: Gary J. Van Berkel, Oak Ridge, FL (US); Mariam S. ElNaggar, Indianapolis, IN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 445 days.

(21) Appl. No.: 13/936,715

(22) Filed: Jul. 8, 2013

(65) Prior Publication Data

US 2013/0294971 A1 Nov. 7, 2013

Related U.S. Application Data

(62) Division of application No. 12/894,872, filed on Sep. 30, 2010, now Pat. No. 8,486,703.

(51) Int. Cl.
*G01N 1/02* (2006.01)
*G01N 1/32* (2006.01)
*G01N 1/38* (2006.01)

(52) U.S. Cl.
CPC .. *G01N 1/02* (2013.01); *G01N 1/32* (2013.01); *G01N 2001/028* (2013.01);
(Continued)

(58) Field of Classification Search
CPC ............ G01N 1/32; G01N 1/02; G01N 1/10; G01N 2001/028; G01N 2001/383; G01N 35/10; G01N 35/1009; G01N 35/1011; Y10T 436/118339; Y10T 436/25; Y10T 436/2575; Y10T 436/117497; B01L 3/02; B01L 3/021; B01L 2200/0673
See application file for complete search history.

(56) References Cited

U.S. PATENT DOCUMENTS

| 3,970,388 A | 7/1976 | Hacker |
| 4,076,420 A | 2/1978 | De Maeyer et al. |

(Continued)

FOREIGN PATENT DOCUMENTS

| DE | 4200497 | 7/1993 |
| DE | 4207074 | 9/1993 |

(Continued)

OTHER PUBLICATIONS

Asano et al., "Self-aspirating atmospheric pressure chemical ionization source for direct sampling of analytes on surfaces and in liquid solutions", RCM (2005) 19(16): 2305-2312.
Becker et al., "Evidence of near-field laser ablation inductively coupled plasma mass spectrometry (NF-LA-ICP-1 MS) at nanometre scale for elemental and isotopic analysis on gels and biological samples", Journal of Analytical Atomic Spectrometry (2006) 21: 19-25.

(Continued)

*Primary Examiner* — Christopher A Hixson
(74) *Attorney, Agent, or Firm* — Fox Rothschild LLP

(57) ABSTRACT

A method of analyzing a chemical composition of a specimen is described. The method can include providing a probe comprising an outer capillary tube and an inner capillary tube disposed co-axially within the outer capillary tube, where the inner and outer capillary tubes define a solvent capillary and a sampling capillary in fluid communication with one another at a distal end of the probe; contacting a target site on a surface of a specimen with a solvent in fluid communication with the probe; maintaining a plug volume proximate a solvent-specimen interface, wherein the plug volume is in fluid communication with the probe; draining plug sampling fluid from the plug volume through the sampling capillary; and analyzing a chemical composition of the plug sampling fluid with an analytical instrument. A system for performing the method is also described.

10 Claims, 11 Drawing Sheets

(52) U.S. Cl.
CPC .... *G01N 2001/383* (2013.01); *Y10T 436/117497* (2015.01); *Y10T 436/118339* (2015.01); *Y10T 436/25* (2015.01); *Y10T 436/2575* (2015.01)

(56) References Cited

U.S. PATENT DOCUMENTS

| | | | |
|---|---|---|---|
| 4,726,487 | A | 2/1988 | Mitri |
| 4,745,809 | A | 5/1988 | Collins et al. |
| 4,865,199 | A | 9/1989 | Zimmer |
| 5,205,473 | A | 4/1993 | Coffin, Sr. |
| 5,271,798 | A | 12/1993 | Sandhu et al. |
| 5,647,990 | A | 7/1997 | Vassarotti |
| 5,783,938 | A | 7/1998 | Munson et al. |
| 6,140,639 | A | 10/2000 | Gusev et al. |
| 6,290,863 | B1 | 9/2001 | Morgan et al. |
| 6,409,832 | B2 | 6/2002 | Weigl et al. |
| 6,478,238 | B1 | 11/2002 | Wachs et al. |
| 6,537,433 | B1 | 3/2003 | Bryning et al. |
| 6,803,566 | B2 | 10/2004 | Van Berkel |
| 6,864,480 | B2 | 3/2005 | Staats |
| 7,129,091 | B2 | 10/2006 | Ismagilov et al. |
| 7,270,948 | B2 | 9/2007 | Demirev |
| 7,445,907 | B2 | 11/2008 | Everett et al. |
| 7,525,105 | B2 | 4/2009 | Kovtoun |
| 7,641,860 | B2 | 1/2010 | Matteo |
| 7,718,958 | B2 | 5/2010 | Shiea et al. |
| 7,762,638 | B2 | 7/2010 | Cruchon-Dupeyrat et al. |
| 2002/0168778 | A1 | 11/2002 | Andrien, Jr. et al. |
| 2003/0193020 | A1* | 10/2003 | Van Berkel .......... H01J 49/165 250/288 |
| 2004/0023410 | A1 | 2/2004 | Stacey |
| 2005/0087122 | A1 | 4/2005 | Ismagliov et al. |
| 2005/0116161 | A1 | 6/2005 | Hafeman et al. |
| 2005/0178959 | A1 | 8/2005 | Lopez-Avila et al. |
| 2005/0276937 | A1 | 12/2005 | Kosth |
| 2007/0138384 | A1 | 6/2007 | Keiser |
| 2007/0224697 | A1 | 9/2007 | Park |
| 2007/0259445 | A1 | 11/2007 | Cedra |
| 2007/0295902 | A1 | 12/2007 | Shea et al. |
| 2008/0003142 | A1 | 1/2008 | Link et al. |
| 2008/0128614 | A1 | 6/2008 | Nikolaev et al. |
| 2008/0131949 | A1 | 6/2008 | Bortolin et al. |
| 2008/0230387 | A1 | 9/2008 | McBride et al. |
| 2008/0308722 | A1 | 12/2008 | Shiea |
| 2009/0000364 | A1 | 1/2009 | Min-Feng |
| 2009/0053689 | A1 | 2/2009 | Oviso et al. |
| 2009/0121124 | A1 | 5/2009 | Schneider |
| 2009/0253210 | A1 | 10/2009 | Kobold et al. |
| 2009/0263440 | A1 | 10/2009 | Kendall |
| 2010/0038529 | A1 | 2/2010 | Sato et al. |
| 2010/0224013 | A1 | 9/2010 | Van Berkel et al. |
| 2010/0294048 | A1 | 11/2010 | McGuire et al. |
| 2011/0100091 | A1 | 5/2011 | Harrup et al. |
| 2011/0259205 | A1 | 10/2011 | Delorme |
| 2012/0119079 | A1 | 5/2012 | Ouyang et al. |

FOREIGN PATENT DOCUMENTS

| | | |
|---|---|---|
| DE | 102004048380 | 4/2006 |
| DE | 102006056929 | 6/2008 |
| GB | 1272409 | 4/1972 |
| GB | 1451599 | 10/1976 |
| JP | 7159293 | 6/1995 |
| JP | 10148605 | 6/1998 |
| JP | 2003035671 | 2/2003 |
| JP | 2006059641 | 3/2006 |
| WO | 0138940 | 5/2001 |

OTHER PUBLICATIONS

Bohn et al., "Field enhancement in apertureless near-field scanning optical microscopy", J Opt Soc AM (Optical Society of America) (2001) 18(12): 2998-3006.

Chen et al., "The irradiation effect of a Nd-YAG pulsed on the Ce02 target in the liquid", Materials Letters (2004) 58: 337-341.
De Serio et al., "Looking at the nanoscale: Scanning near-field optical microscopy", Trends in Analytical Chemistry (2003) 22(2): 70-77.
Douglas et al., "Laser ablation of a sample in liquid—LASIL", J Anal at Spectrum (2011) 26: 1294-1301.
Dunn, "Near-field scanning optical microscopy", Chem Rev (1999) 99: 2891-2927.
Eskin, "Just a day at the beach", Chicago Tribune (2002), Retrieved from http://articles.chicagotribune.com/2002-06-02/features/0206020498_1_lemon-zest-lemon-juice-cups.
Final Office Action mailed on Jan. 17, 2013 in U.S. Appl. No. 13/102,606. (23 pages).
Inouye, "Apertureless metallic probes for near-field microscopy", Topics Appl Phys (2001) 81: 29-46.
International Search Report mailed on Jan. 12, 2011 in PCT Application No. PCT/US2011/035604.
International Search Report mailed on Dec. 1, 2011 in PCT Application No. PCT/US2011/053799.
International Search Report mailed on Mar. 12, 2012 in PCT Application No. PCT/US2011/054622.
"Liquid-phase pulsed laser ablation", Chapter 2 (p. 33-51).
Leung et al., "Transmission studies of explosive vaporization of a transparent liquid film on an opaque solid surface induced by Excimer-Laser-Pulsed Irradiation", J Appl Phys (1992) 72(6): 2256-2263.
Meunier et al., "Laser processing laboratory. Colloidal metal nanoparticles synthesized by femtosecond laser ablation in liquids", Retrieved on Oct. 7, 2013, from http://www.jlab.org/FEL/LPC/05lpc-meunier.pdf (25 pages).
Muravitskaya et al., "Laser ablation in liquids as a new technique of sampling in elemental analysis of solid materials", Spectrochimica Acta Part B (2009) 64: 119-125.
Novotny et al., "Near-field optical microscopy and spectroscopy with pointed probes", Annu Rev Phys Chem (2006) 57: 303-331.
Reddy, "Solid dispersions", Retrieved on Oct. 7, 2013, from http://www.authorstream.com/Presentation/robin_vinnu-623593-solid-dispersions/ (video).
Schmid et al., "Methods for molecular nanoanalysis", Chimia (2006) 60(11): 783-788.
Schmitz et al., "Towards nanoscale molecular analysis at atmospheric pressure by a near-field laser ablation ion trap/time-of-flight mass spectrometer", Analytical Chemistry (2008) 80(17): 6537-6544.
Song et al., "Reactions in droplets in microfluidic channel", Angew. Chem. Int. Ed. (2006) 45: 7336-7356.
Stockle et al., "Nanoscale atmospheric pressure laser ablation-mass spectrometry", Analytical Chemistry (2001) 73(7): 1399-1402.
Tsuji et al., "Microsecond-resolved imaging of laser ablation at solid-liquid interface: Investigation of formation process of nano-size metals colloids", Applied Surface Science (2004) 229: 365-371.
Van Berkel et al., "Established and emerging atmospheric pressure surface sampling/ionization techniques for mass spectrometry", J. Mass Spectrom. (2008) 43: 1161-1180.
Van Berkel et al., "Thin-layer chromatography and electrospray mass spectrometry coupled using a surface sampling probe", Anal. Chem. (2002) 74: 6216-6223.
Yan et al., "Hollow nanoparticle generation on laser-induced cavitation bubbles via bubble interface pinning", Appl Phys Lett (2010) 97: 124106-1-3.
Yang, "Laser ablation in liquids: Applications in the synthesis of nanocrystals", Progress in Materials Science (2007) 52: 648-698.
Yasuo et al., "Laser ablation in a liquid medium as a technique for solids sampling", Journal of Analytical Atomic Spectrometry (1991) 6: 541-544.
Yavas et al., "Bubble nucleation and pressure generation during cleaning surfaces", Appl Phys A (1997) 64: 331-339.
Zeisel et al., "Pulsed laser-induced deportation and optical imaging on a nanometer scale with scanning near-field microscopy using chemically etched fiber tips", Appl Phys Letter (1996) 68(18): 2491-2492.

* cited by examiner

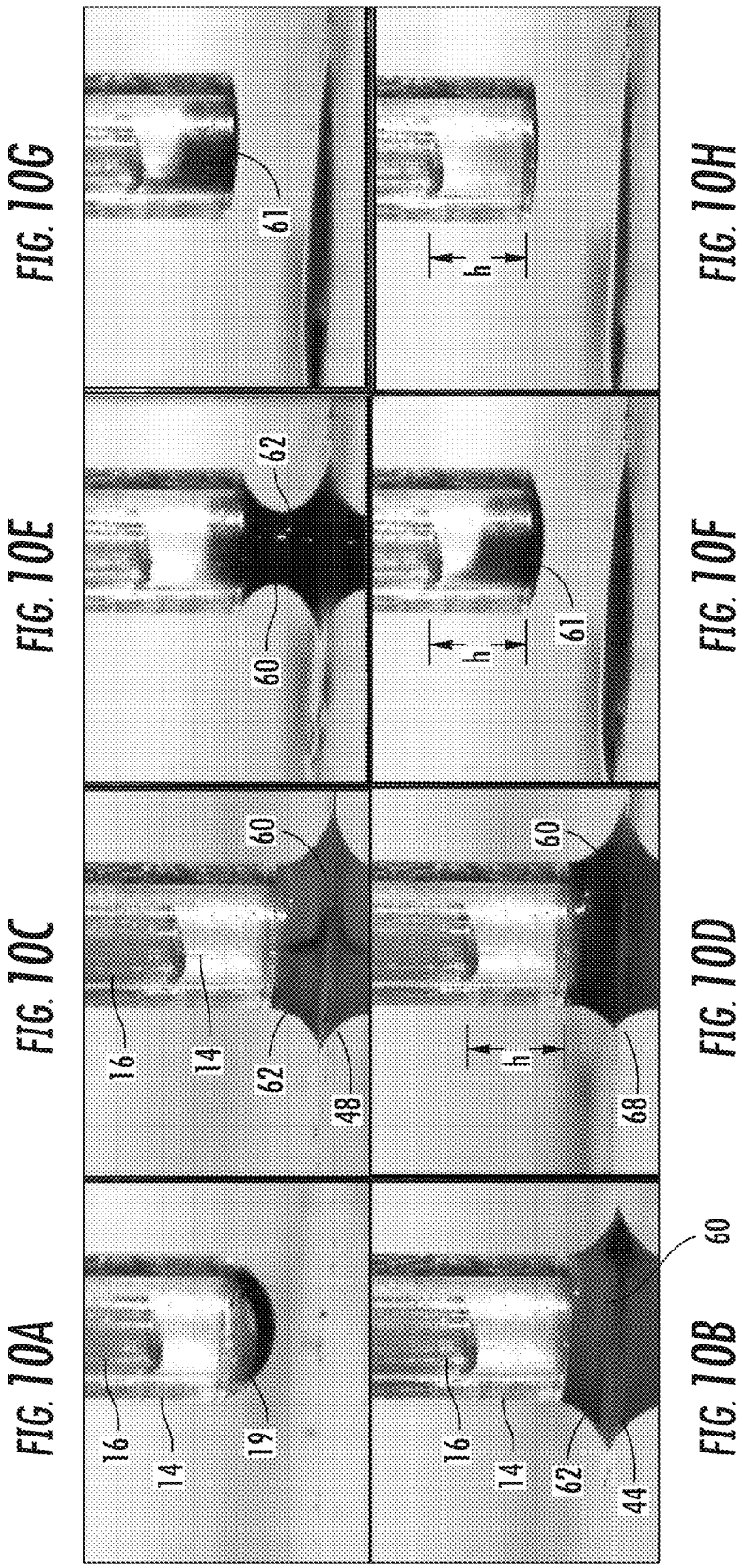

SURFACE SAMPLING CONCENTRATION AND REACTION PROBE WITH CONTROLLER TO ADJUST SAMPLING POSITION

CROSS REFERENCE TO RELATED APPLICATIONS

This application is a divisional of application of U.S. Nonprovisional application Ser. No. 12/894,872, filed Sep. 30, 2010, the disclosure of which is incorporated fully by reference.

STATEMENT REGARDING FEDERALLY SPONSORED RESEARCH

This invention was made with government support under Contract No. DE-AC05-00OR22725 awarded by the U.S. Department of Energy. The government has certain rights in this invention.

FIELD OF THE INVENTION

This invention is drawn to systems and methods for surface sampling in general, and for reacting and concentrating surface samples in the probe during processing.

BACKGROUND OF THE INVENTION

Advances in analytical technology have pushed the limits of human understanding of chemical and physical phenomena. New tools create the opportunity for the new discoveries. Currently available techniques, such as liquid microjunction probes, allow analysis of the chemical composition of surfaces. However, convention liquid microjunction probes can be limited due to the cross-sectional area of the probe itself and the extraction rate of analytes present in the surface being analyzed. Thus, there is room for improvement in surface extraction technology.

SUMMARY OF THE INVENTION

A method and system for analyzing a chemical composition of a specimen is described. The method can include providing a probe comprising an outer capillary tube and an inner capillary tube disposed co-axially within the outer capillary tube, such that the inner and outer capillary tubes define a solvent capillary and a sampling capillary in fluidic communication with one another at a distal end of the probe. A target site on a surface of a specimen can then be contacted with a solvent in fluid communication with the probe. A plug volume in fluid communication with the probe can be maintained proximate a solvent-specimen interface. The sampling fluid can then be drained from the plug volume through the sampling capillary and a chemical composition of the plug sampling fluid can be analyzed with an analytical instrument. The contacting step can include forming a junction between a distal end of the probe and a surface of the target site.

The draining can be achieved by modifying a sampling characteristic of the probe. The sampling characteristic that is modified can be selected from (i) decreasing a distance between a tip of the outer capillary and a tip of the inner capillary, (ii) increasing the sampling capillary flow rate relative to the solvent capillary flow rate, and (iii) breaking a liquid junction between the specimen and the solvent in fluid communication with the probe. During the maintaining step, the capillary ratio (h/H) can exceed a capillary ratio threshold, wherein h is a distance between a tip of said outer capillary tube and a tip of said inner capillary tube, and H is an inner diameter of the outer capillary tube. During the draining step, the capillary ratio (h/H) can be equal to the capillary ratio threshold or less.

The method can include repeating the contacting, maintaining, draining and analyzing steps for each of a plurality of target sites on the specimen. A property of a chemical component for each of the plurality of target sites can then be plotted.

The method can include providing a solvent that includes a reactant selected to react with a target analyte that is sought to be analyzed. The method can also include translating the probe from the target site to a second target site while the solvent remains in fluidic communication with the probe and with the surface of the specimen. The solvent can remain in fluid communication with each of the target site and the second target site for at least 5 seconds.

The invention is also drawn to a system comprising for analyzing a chemical composition of a specimen. The system can include the dual capillary probe, an adjuster coupled to the outer capillary tube and the inner capillary tube for moving a tip of the outer capillary tube and an tip of the inner capillary tube longitudinally relative to one another. The system can also include a controller that is communicatively coupled to the adjuster and is configured for actuating the adjuster to impart relative longitudinal motion between the outer capillary tube and the inner capillary tube. The system can also include an analytical instrument for determining a chemical composition of an analyte, wherein a sampling capillary is in fluid communication with the analytical instrument.

BRIEF DESCRIPTION OF THE DRAWINGS

A fuller understanding of the present invention and the features and benefits thereof will be obtained upon review of the following detailed description together with the accompanying drawings, in which:

FIGS. 10A-H are time lapse sequences showing the formation a plug volume over a target site and a reactant spot and then the draining of the plug sampling liquid produced by the sequence.

DETAILED DESCRIPTION OF THE INVENTION

Figure 1:
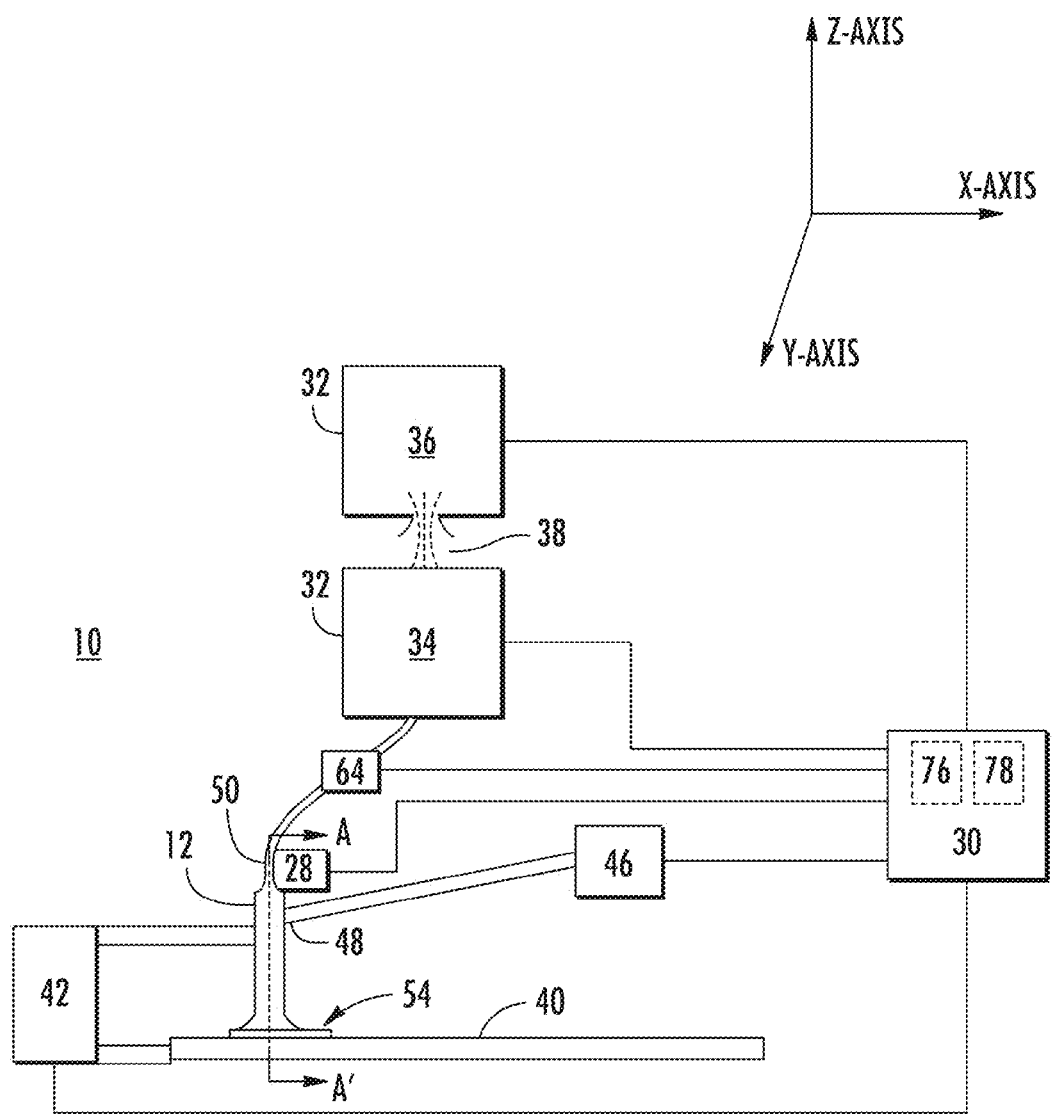
FIG. 1 is a schematic showing a system according to the invention.

The present invention is directed to systems and methods for chemical composition analysis of the surface of a specimen. In particular, the systems and methods described herein are capable of maintaining a plug volume of fluid proximate to the surface being analyzed in order to concentrate and/or react analytes from the surface. In effect, the plug volume serves as a nanoscale reactor and provides functionality not otherwise possible using conventional liquid microjunction probes, whether contact or non-contact. The systems and methods described herein can also include providing chemical mapping of the surface of the specimen.

It is noted that like and corresponding elements mentioned herein and illustrated in the figures are generally referred to by the same reference numeral. It is also noted that proportions of various elements in the accompanying figures are not drawn to scale to enable clear illustration of elements having smaller dimensions relative to other elements having larger dimensions.

Figure 11:
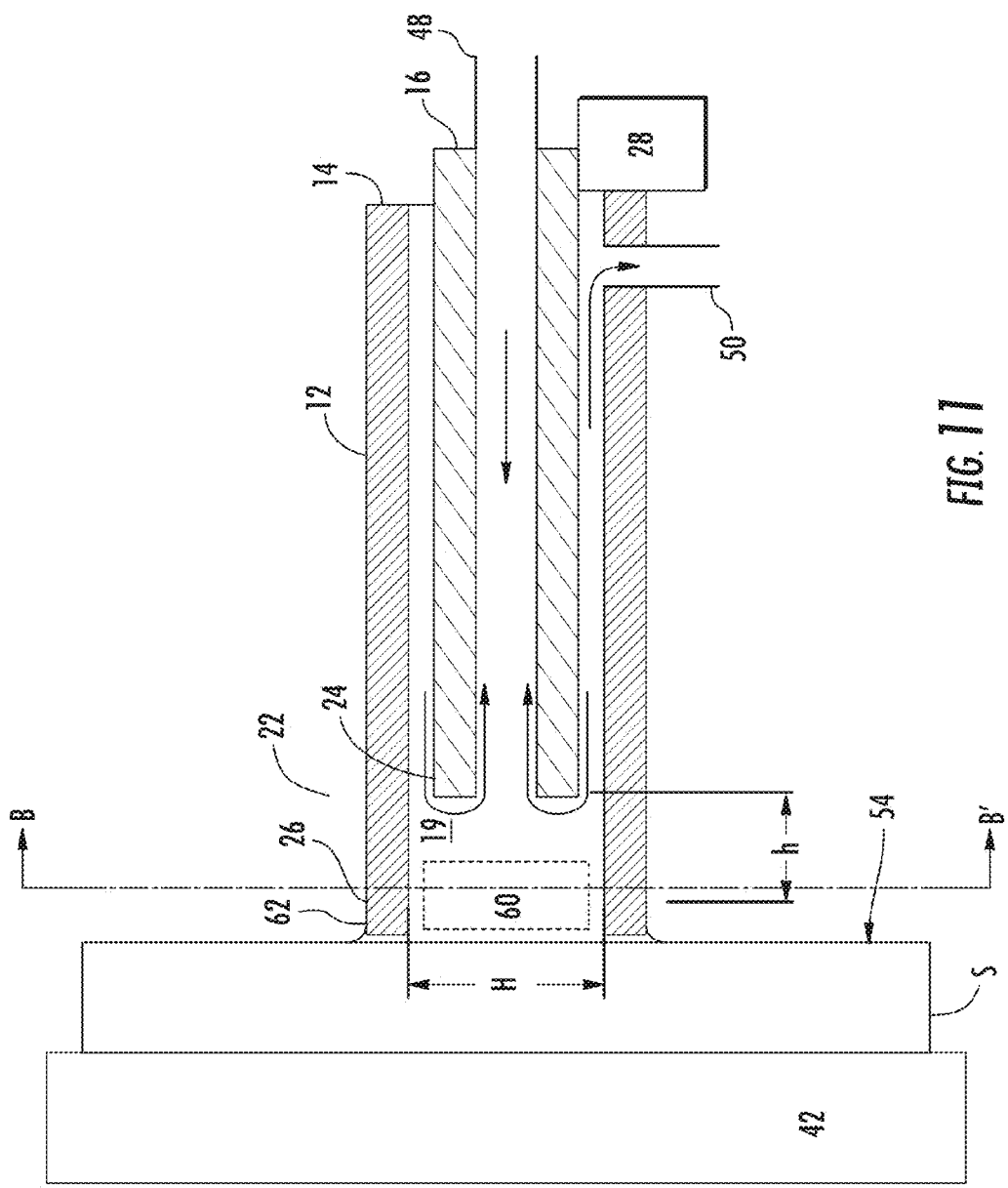
FIG. 11 is a cross-section taken along cut-line A-A' showing a probe according to the invention where the outer capillary is the sampling capillary and the inner capillary is the solvent capillary.

As shown in the Figures, the system 10 for analyzing the chemical composition of a specimen can include a probe 12 that includes an outer capillary tube 14 and an inner capillary tube 16 disposed co-axially within the outer capillary tube 14. The inner and outer capillary tubes 16, 14 can define a solvent capillary 18 and a sampling capillary 20 in fluidic communication with one another at a distal end 22 of the probe 12. In general, this fluidic communication is facilitated because the inner capillary tube tip 24 is recessed within the outer capillary tube 26. As shown in FIGS. 2-4 and 7-10, the inner capillary tube 16 can define the sampling capillary 20 and the annular space between the inner capillary tube 16 and the outer capillary tube 14 can define the solvent capillary 18. Alternately, as shown in FIG. 11, the inner capillary tube 16 can define the solvent capillary 18 and the annular space between the inner capillary tube 16 and the outer capillary tube 14 can define the sampling capillary 20.

The dimensions of an inner diameter of the inner capillary tube 16 can be from 1 micron to 1 mm, e.g., 200 microns. Typical dimensions of the outer diameter of the inner capillary tube 16 can be from 100 microns to 3 or 4 centimeters, e.g., 360 microns. Typical dimensions of the inner diameter of the outer capillary tube 14 can be from 100 microns to 3 or 4 centimeters, e.g., 450 microns. Typical dimension of an outer diameter of the outer capillary tube 14 can be from 150 microns to 3 or 4 centimeters, e.g., 950 microns. The cross-sectional areas of the inner capillary tube 16 and/or the outer capillary tube 14 can be circular, elliptical, superelliptical (i.e., shaped like a superellipse), or even polygonal.

The system 10 can also include an adjuster 28 coupled to the outer capillary tube 14 and the inner capillary tube 16. The adjuster 28 can be adapted for moving the outer capillary tube tip 24 and the inner capillary tube tip 26 longitudinally relative to one another. The adjuster 28 can be any device capable of moving the outer capillary tube 14 relative to the inner capillary tube 16. Exemplary adjusters 28 can be motors including, but are not limited to, electric motors (e.g., AC motors, DC motors, electrostatic motors, servo motors, etc.), hydraulic motors, pneumatic motors, translational stages, and combinations thereof. As used herein, "longitudinally" refers to an axis that runs the length of the probe 12, and the inner and outer capillary tubes 16, 14 can be arranged coaxially around a longitudinal axis of the probe 12, as shown in FIGS. 2-4 and 7-10.

Since their inception, dual-capillary sampling probes 12 have been designed and used for continuous sampling of a surface. The inventors have unexpectedly discovered that it is possible to form a plug volume 60 at the distal end 22 of the dual-capillary sampling probe 12, such as those shown in FIGS. 2-4 and 7-10, by using the proper sampling characteristics. Thus, the inventors have developed unique probes 12 and methods of using these unique probes 12 that enable users to maintain the plug volume 60 with the proper sampling characteristics and to drain the plug sampling fluid 61 from the plug volume 60 using the proper sampling characteristics.

As used herein, a "plug volume" is a volume of liquid that remains relatively localized with limited liquid loss or exchange with the surrounding liquid. For example, the liquid loss or exchange rate from a plug volume 60 to the surrounding liquid 19 can be less than a "plug volume loss threshold," which can be 20 vol-% per minute or less, or 10 vol-% per minute or less, or 7.5 vol-% per minute or less, or 5 vol-% per minute or less. It is to be understood that the term "plug volume" refers to the volume within the solvent 19 that exhibits the localized fluid properties described above and does not include the liquid lost to the surrounding solvent 19. Exemplary plug volumes include, but are not limited to, an eddy layer and a stagnant layer.

As used herein, "plug sampling fluid" refers to the liquid that is contained within the plug volume 60 when the draining step begins, i.e., refers to the fluid that is drained from the plug volume 60 and transferred to the analytical instrument 32 for evaluation. In general, the draining begins when the liquid loss or exchange from the plug volume 60 to the surrounding solvent 19 exceeds the plug volume loss threshold. For example, the draining can begin when the exchange with the surrounding liquid 19 first exceeds 5 vol-% per minute, first exceeds 7.5 vol-% per minute, or first exceed 10 vol-% per minute, or first exceed 20 vol-% per minute.

Because the plug volume 60 is proximate to the surface 54 of the specimen (S) and the liquid 19 within the plug volume 60 is exchanged with the surrounding fluid 19 slowly, if at all, it is possible to obtain analyte concentrations within the plug volume 60 that are much higher than is using conventional liquid junction sampling probes and/or techniques. Similarly, because the liquid 19 within the plug volume 60 is exchanged with the surrounding fluid 19 slowly, if at all, the analyte contained within the plug volume 60 can be reacted with reactants, catalysts or both, that are also in the plug volume 60. In this sense, the plug volume 60 can function as a reactor to produce a plug sampling volume 61 for improved analysis by the analytical instruments 32.

Thus, the systems 10 and methods described herein enable users to increase analyte concentration in the plug volume 60 prior to dispensing the plug sampling liquid 61 to the analytical instrument 32. Similarly, the systems 10 and methods described herein enable users to utilize the plug volume 60 like a nano-reactor and react the analyte, which is generally solubilized, with reactants or catalysts that may be present in the solvent 19 stream or on a surface 54 of the specimen (S).

As used herein, "sampling characteristics" are probe variables that can be manipulated during the sampling processes described herein. Exemplary sampling characteristics include (i) changing, i.e., increasing or decreasing, a distance (h) between an outer capillary tip 26 and an inner capillary tip 24, (ii) changing the flow rate in the sampling capillary 20 relative to the flow rate in the solvent capillary 18, and (iii) breaking a liquid junction 62 between the surface 54 of the specimen (S) and the solvent 19 in fluidic communication with the probe 12. In particular, the plug volume 60 can be drained by (i) decreasing a distance (h) between an outer capillary tip 26 and an inner capillary tip 24, (ii) increasing the flow rate in the sampling capillary 20 relative to the flow rate in the solvent capillary 18, (iii) breaking a liquid junction 62 between the surface 54 of the specimen (S) and the solvent 19 in fluidic communication with the probe 12, or a combination thereof.

Figure 2:
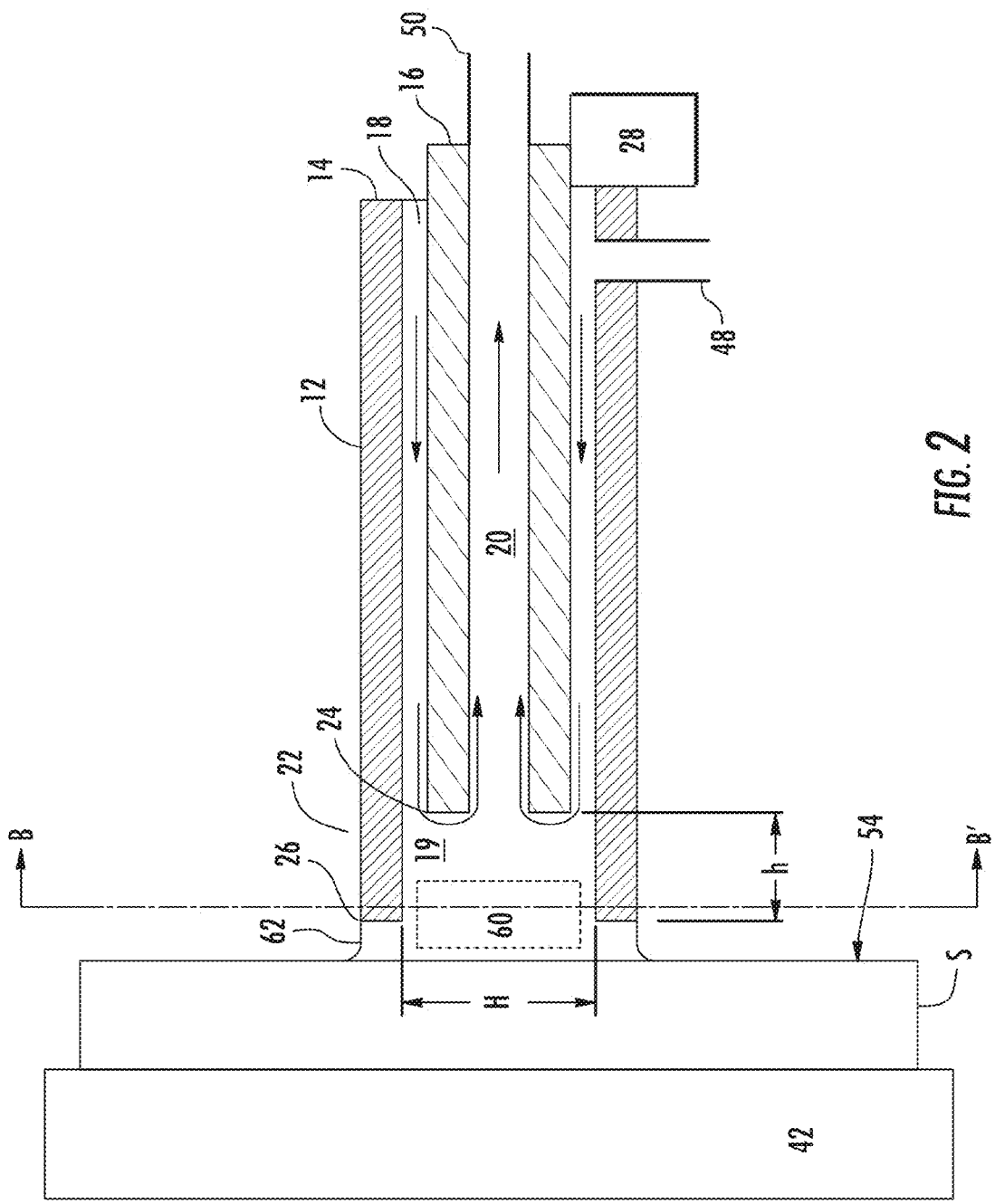
FIG. 2 is a cross-section of the probe shown in FIG. 1 taken along cut line A-A' where the capillary ratio exceeds the plug ratio threshold and the junction is a liquid junction.
Figure 3:
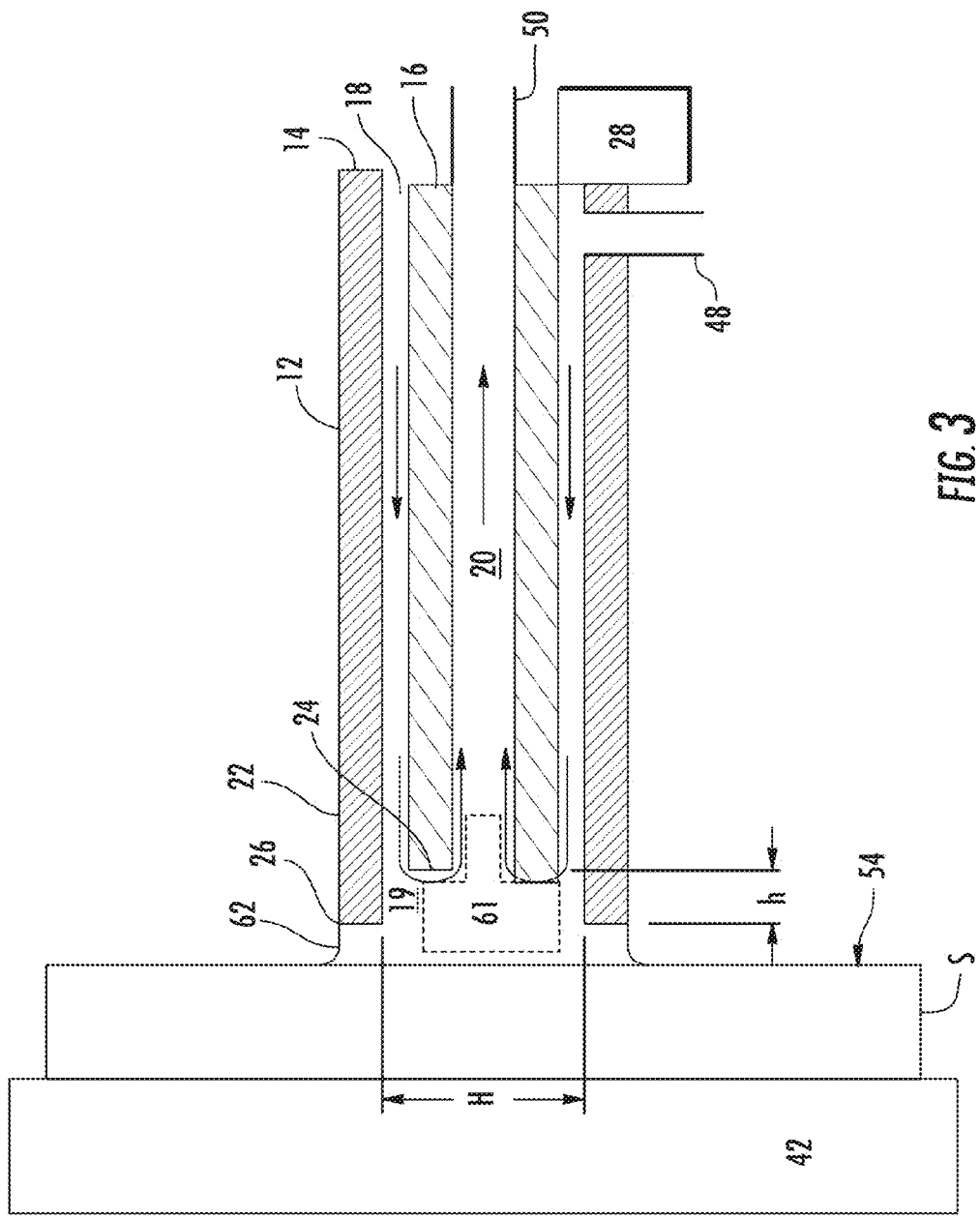
FIG. 3 is a cross-section of the probe shown in FIG. 1 taken along cut line A-A' where the capillary ratio is less than the plug ratio threshold and the junction is a liquid junction.
Figure 4:
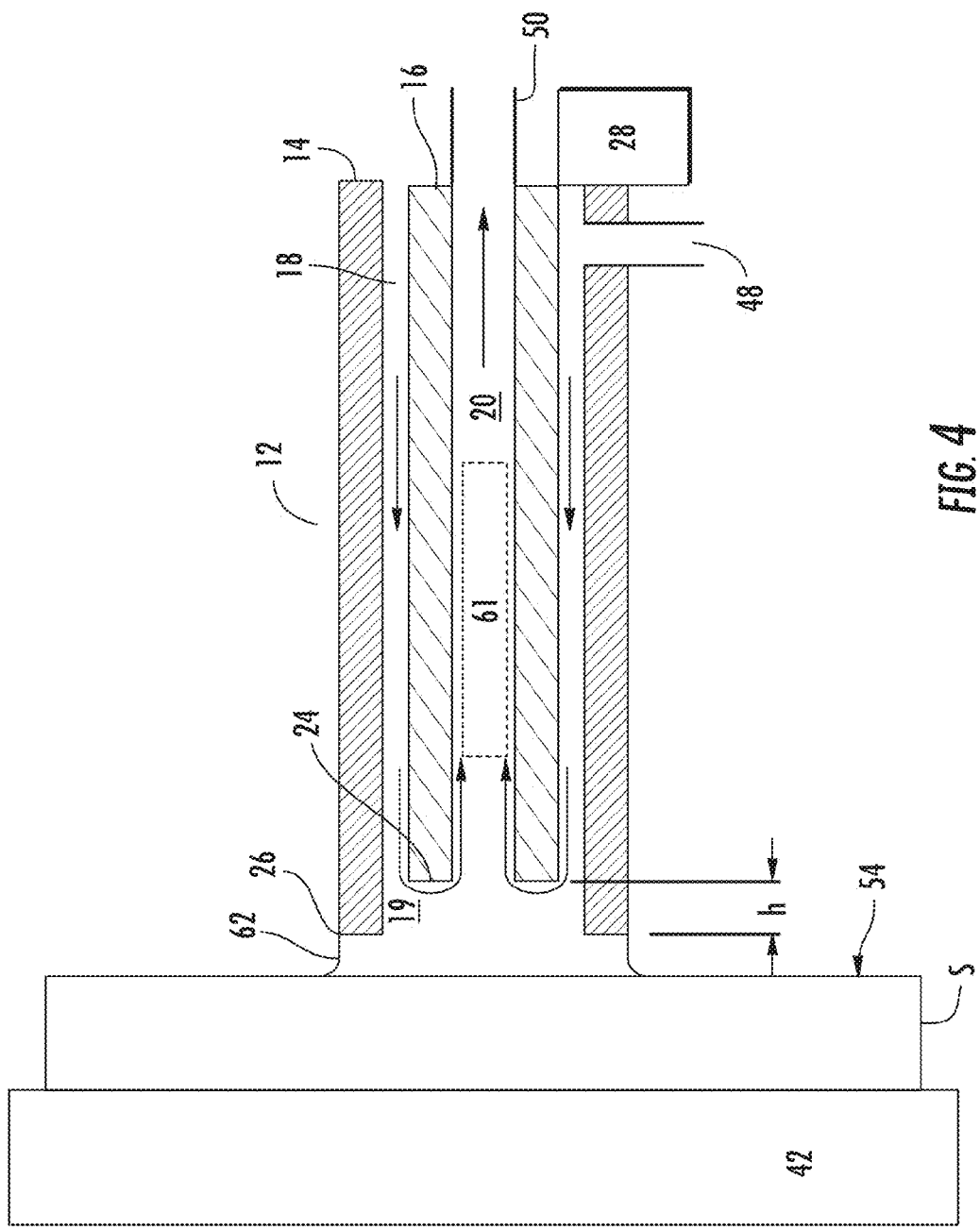
FIG. 4 is a cross-section of the probe shown in FIG. 1 taken along cut line A-A' where the capillary ratio is less than the plug ratio threshold and the junction is a liquid junction.

In one example using a dual-capillary probe 12 as shown in FIGS. 2-4, the inner diameter (H) of the outer capillary tube 14 can be 200 µm and a lateral distance (h) between the inner capillary tip 24 and the outer capillary tip 26 can be 400 µm, when a liquid micro-junction 62 is formed between the probe and the surface 54 of the specimen (S). As shown schematically in FIG. 2 (not to scale), this can form a plug volume 60. The adjuster 28 can then be actuated so that the lateral distance (h) between the inner capillary tip 24 and the outer capillary tip 26 is reduced, e.g., 200 µm, as shown schematically in FIG. 3 (not to scale). This reduction in the lateral distance (h) between the inner capillary tip 24 and the outer capillary tip 26 can be sufficient to drain the plug sampling liquid 61 from the plug volume 60 as shown in FIGS. 3 & 4 (not to scale).

The plug volume 60 can be formed by adjusting the lateral position of the inner capillary tube 16 and the outer capillary tube 14 such that a capillary ratio (h/H) crosses the plug ratio threshold, e.g., a capillary ratio of at least 1.0, or at least 1.25, or at least 1.5 or at least 1.75 or at least 2.0. In the capillary ratio, h is the lateral distance between the outer capillary tube tip 26 and the inner capillary tube tip 24, and H is an inner diameter of the outer capillary tube 14. Similarly, the plug volume 60 can be drained by adjusting the lateral position of the inner capillary tube 16 and the outer capillary tube 14 such that the capillary ratio (h/H) crosses the plug ratio threshold, e.g., is reduced to 2.0 or less, or less than 1.75, or less than 1.5, or less than 1.25, or less than 1.0.

As used herein, the "plug ratio threshold" is the capillary ratio at which a plug volume 60 transitions to a non-plug volume or vice versa. As will be understood, the value of the plug ratio threshold can vary depending on the values of other sampling characteristics, such as the specific diameter of the inner capillary 16, the flow rate of the sampling capillary 20 and the flow rate of the solvent capillary 18. Thus, the controller 30 can be configured to actuate the adjuster 28 to position the inner capillary tip 24 and the outer capillary tip 26 to cross the plug ratio threshold in order to (i) form a plug volume 60, or (ii) release the plug sampling fluid 61 from the plug volume 60.

The system 10 can also include an analytical instrument 32 for determining a chemical composition of an analyte as a target site 44 on a specimen (S) being analyzed. The solvent capillary 18 can be in fluidic communication with a solvent pump 46 via a solvent inlet 48. The sampling capillary 20 can be in fluid communication with the analytical instrument 32 via a sampling outlet 50.

A sampling pump 64 can be provided in order to control the output rate from the sampling capillary 20. This enables the user to control the flow rates at the sampling capillary output 50 and the solvent capillary input 48, which can be the same or different flow rates. Although shown separately, the sampling pump 64 can be incorporated into the probe 12 or any downstream device, such as an analytical instrument 32. The pumps 46, 64 can be any form of pump including, but not limited to velocity pumps, buoyancy pumps, syringe pumps, positive displacement pumps, venturi pumps, and gravity pumps. Of particular interest, the pumps 46 and 64 can be syringe pumps, positive displacement pumps, nebulization or electrospraying devices, or chambers with sufficient pressure differentials to induce fluid flow.

In one example, the plug volume 60 can be interrupted or broken by turning off the solvent pumping device 46 while maintaining a constant flow rate by the sampling aspirating device 64. Alternately, a plug volume 60 can be (a) interrupted or broken by increasing the flow rate of both the solvent pumping device 46 and the sampling aspirating device 64, and (b) maintained or produced by decreasing the flow rate of both the solvent pumping device 46 and the sampling aspirating device 64.

Both the solvent pumping device 46 and the sampling aspirating device 64 can be in communication with the controller 30. The controller 30 can be configured to control the solvent pumping device 46, the sample aspirating device 64, or both in order to produce any of the effects described herein.

In some embodiments, the system 10 can include an ionization source 34 and a mass spectrometer 36, where the ionization source 34 and the mass spectrometer 36 are arranged so that an ionized analyte 38 emitted by the ionization source 34 is directed into the mass spectrometer 36.

The analytical instrument 32 can be any instrument utilized for analyzing analyte solutions. Exemplary analytical instruments include, but are not limited to, mass spectrometers, ionization sources, spectroscopy devices, separation methods, and combinations thereof. Exemplary ionization sources include, but are not limited to electrospray ionization, atmospheric pressure chemical ionization, atmospheric pressure photo-ionization or inductively coupled plasma. Exemplary separation methods include, but are not limited to liquid chromatography, solid phase extraction, HPLC, capillary electrophoresis, or any other liquid phase sample cleanup or separation process. Exemplary mass spectrometers ("MS") include, but are not limited to, sector MS, time-of-flight MS, quadrupole mass filter MS, three-dimensional quadrupole ion trap MS, linear quadrupole ion trap MS, Fourier transform ion cyclotron resonance MS, orbitrap MS and toroidal ion trap MS. Exemplary ionization sources are electrospray ionization, atmospheric pressure chemical ionization, and combinations thereof, i.e., electrospray chemical ionization (ESCi).

The system 10 can also include a specimen stage 40 for supporting a specimen (S) and a stepper mechanism 42 configured to provide relative motion between the specimen stage 40 and the probe 12. The stepper mechanism 42 can be communicatively coupled to the controller 30. The controller 30 being configured for actuating the stepper to sequentially articulate the probe 12 and the specimen stage 40 along a predetermined sampling path 52 comprising a plurality of target sites 44.

As used herein, a stepper mechanism has its standard meaning in the art and should be understood to include any device or combination of devices for changing the relative position between the probe 12 and the sample stage 40 or the specimen (S) supported thereon. For example, the sample stage 40 can be coupled to the stepper mechanism 42 and move the sample stage 40 laterally (X-axis), transversely (Y-axis), and vertically (Z-axis) along the sampling path 52. Alternately, the probe 12 can be mounted to the stepper 40 and can move the probe 12 laterally, transversely and vertically along the sampling path 52.

Figure 5:
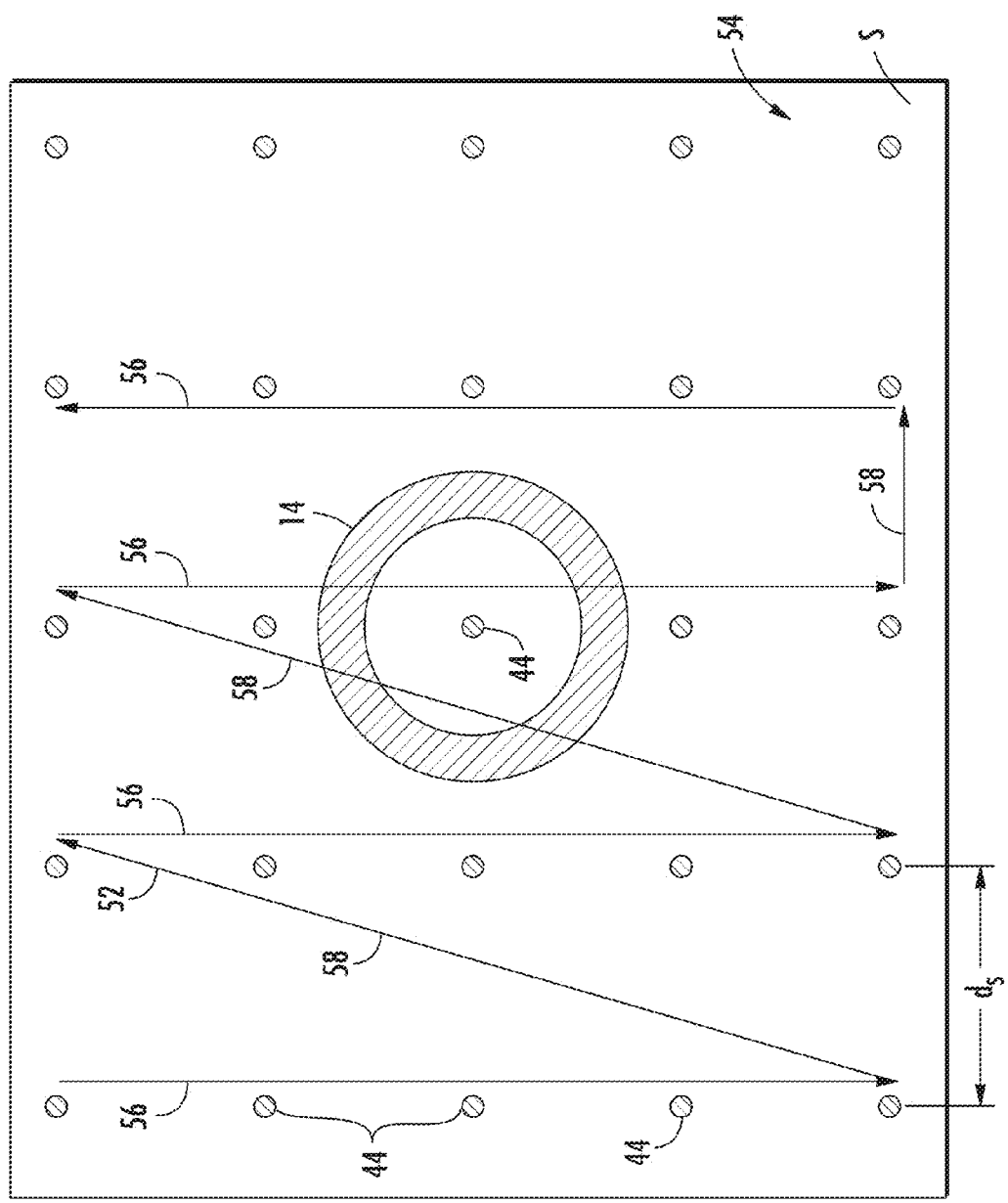
FIG. 5 is a cross-section of the system shown in FIG. 2, taken along cut line B-B'.
Figure 6:
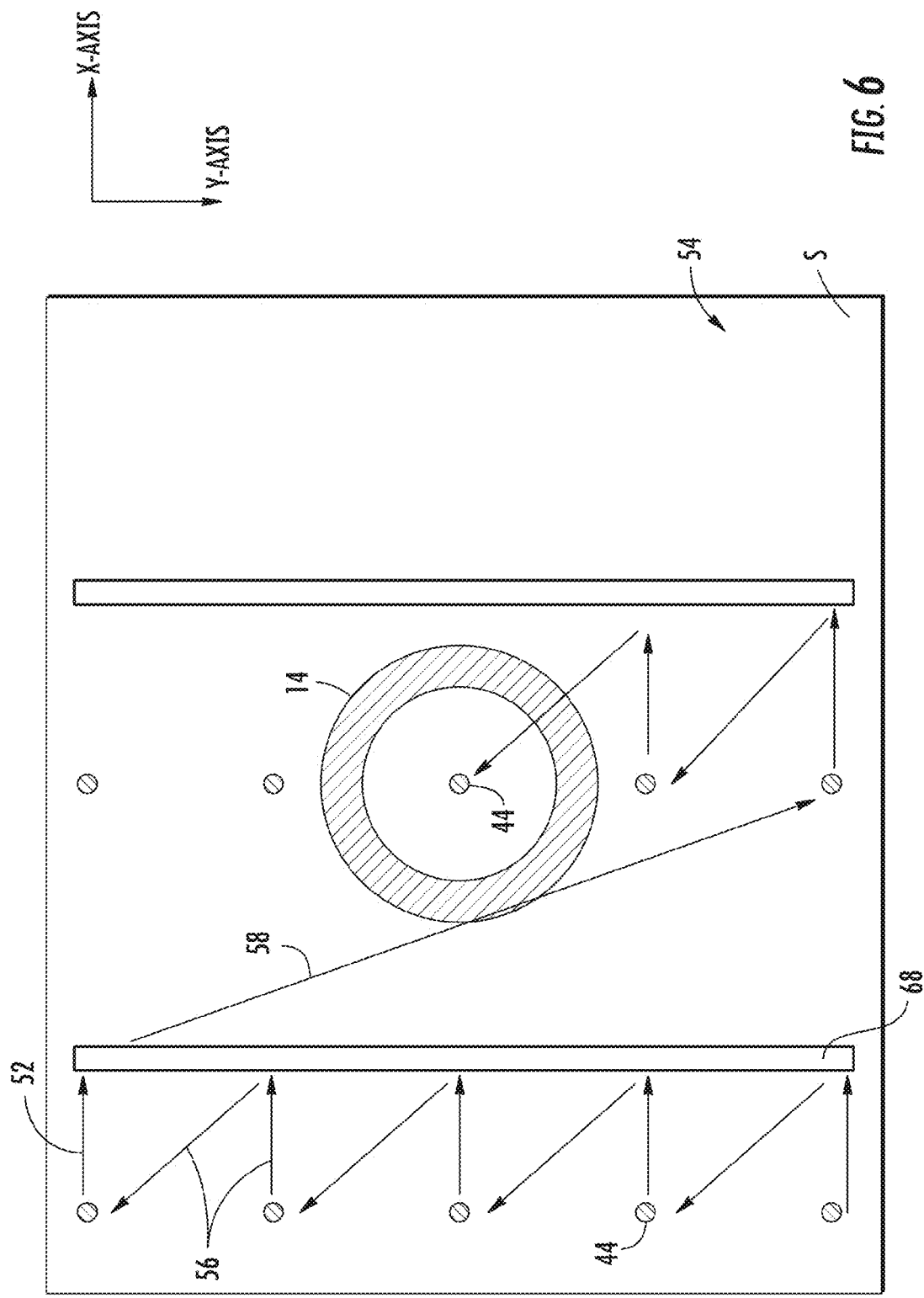
FIG. 6 is a cross-section of a variation of the system shown FIG. 5, taken along cut line B-B' in FIG. 2.
Figure 7:
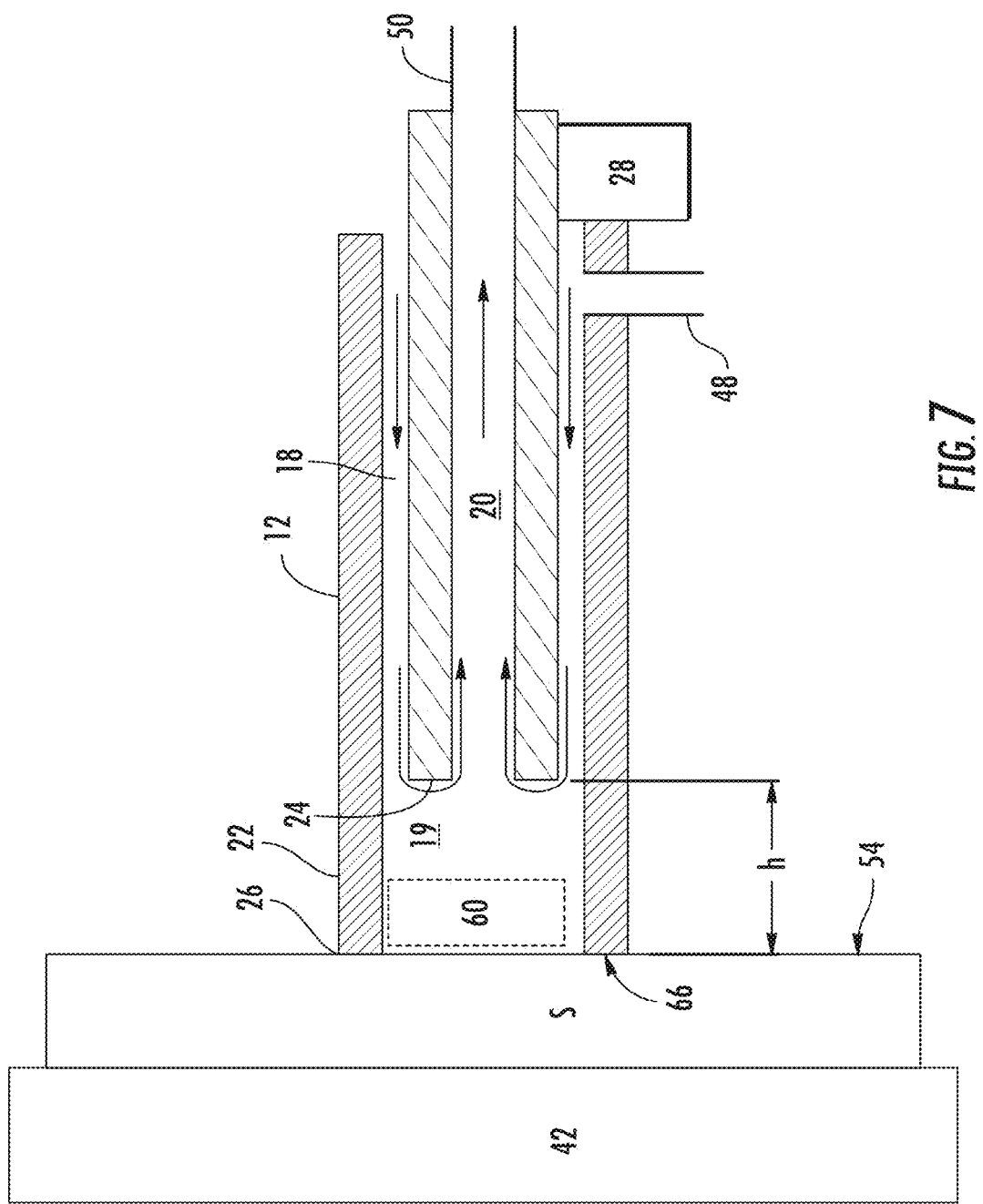
FIG. 7 is a cross-section of the probe shown in FIG. 1 taken along cut line A-A' where the capillary ratio exceeds the plug ratio threshold and the junction is a contact junction.

As shown in FIGS. 5 & 6, a sampling path 52 can be a sampling regime that includes a plurality of target sites 44. FIGS. 5 & 6 only show the lateral and transverse component of the sequence for sampling the target sites 44 along the sampling path 52; however, the sampling path 52 can also include a vertical component. For example, the probe 12 and a first target site 44 can be brought into contact either directly or via a liquid micro-junction for purposes of dissolving an analyte at the first target site 44, as shown in FIGS. 7 & 2, respectively, and can then be separated while the stepper 42 repositions the probe 12 above a second target site 44.

The contacting can occur with the probe 12 in direct contact, i.e., via a contact junction 66, with the surface 54 of the specimen (S), i.e., on or proximate to the target site 44. The articulation by the stepper 42 between sequential target sites 44 can occur with the probe 12 (i) in direct contact and liquid communication with a surface 54 of the specimen (S), (ii) in liquid communication but not direct contact with a surface 54 of the specimen (S), or (iii) neither contacting nor in liquid communication with a surface 54 of the specimen (S). Similarly, the contacting step where the analyte is transferred to the solvent 19 can occur with the probe 12 (i) in direct contact and liquid communication with a surface 54 of the specimen (S) or (ii) in liquid communication but not direct contact with a surface 54 of the specimen (S), i.e., coupled via a liquid micro-junction. The controller 30 can be configured for causing the stepper mechanism 42 to perform each of the sampling sequences described above, or anywhere herein.

In some examples, the target sites 44 can be sampling lines 56. In general, the plurality of sampling lines 56 will be parallel and spaced apart by a distance ($d_s$). In such an embodiment, the specimen (S) can be contacted, i.e., sampled, along an entire sampling line 56. The probe 12 and the sample stage 40 will then travel along a relocating path 58 prior to sampling the next sampling line 56 along the sampling path 52. In such an embodiment, the sampling path 52 can include a plurality of sampling lines 56 and relocating paths 58, as shown in FIG. 5.

The sampling path 52 can be an array of regularly spaced target sites 44. As used herein, "regular spacing" and "regularly spaced" are used interchangeably and refer to spacing where the distance between adjacent target sites 44 in a line is equal or approximately equal along the length of the line, as shown in FIG. 5. Regular spacing also refers to instances where the same target site is part of two or more lines with regular spacing, which is also shown in FIG. 5. Of interest, the distance between adjacent target sites 36 or adjacent sampling lines 56 can be 100 μm or less, or 50 μm or less, or 25 μm or less, or 10 μm or less, or 5 μm or less.

The system can also include using the analytical instrument 32 to determine a chemical composition of an analyte desorbed at each of the plurality of target sites 44 included as part of the sampling path 52. The chemical composition data can then be used to generate and display a multi-dimensional plot.

The data from each of the target sites 44 can be stored in a computer readable storage, such as are known in the art. The data can be compiled to form a two-dimensional map, or surface, of the composition of the specimen by plotting the data according to the position of the array of target sites from which the data was obtained. The data can be displayed on an output device, such as a monitor, printer, smartphone or the like.

The system 10 can also include a controller 30 communicatively coupled to the adjuster 28. The controller 30 can be configured for actuating the adjuster 28 to impart relative longitudinal motion between the outer capillary tube 14 and the inner capillary tube 16.

The controller 30 can also be configured for causing the system 10 components described herein to carry out any of the method steps or processes described herein. For example, the controller 30 can be configured to cause the stepper mechanism 42 to sequentially articulate the probe 12, the sample stage 40, or both, along a sampling path 52 that includes a plurality of target sites 44. The controller 30 can also be configured for maintaining, then draining a plug volume 60 from the distal end 22 of the probe 12. The controller 30 can also coordinate the plug volume 60 maintaining and draining steps with intermediate repositioning steps required to produce plug sample liquid 61 for each target site 44 along the sampling path 52.

The controller 22 can include a computer readable storage 76 in communication with a processor 78. The computer readable storage 76 can include computer executable instructions for carrying out the methods described herein. The processor 78 can be configured to execute the computer executable instructions stored on the computer readable storage 76. The controller 22 can be in communication with the stepper mechanism 42, the adjuster 28, the analytical instrument 32, the solvent pump 46 and/or the sampling pump 64 described herein. In addition, although shown as a single box that includes a single computer readable storage 76 and a single processor 78, it should be understood that the controller 22 can be spread across multiple devices and can include multiple computer readable storages and processors.

As used herein, sequentially articulate refers to automatically moving the probe 12, the sample stage 40, or both along the sampling path 52 to a plurality of target sites 44. In some instances this articulation can be continuous while in others there will be intermittent pauses. For example, the articulation may be paused while the analyte is reacted or concentrated in the plug volume 60 in order to ensure an adequate amount of analyte is present in the plug sampling liquid 61 or to provide adequate separation between ionized analyte 38 samples being fed to an analytical instrument 32, such as a mass spectrometer 36.

A method of analyzing a chemical composition of a specimen is also described. The method can include providing a dual-capillary surface sampling probe 12 as described herein; contacting a target site on a surface of a specimen with a solvent in fluid communication with the probe 12; maintaining a plug volume 60 proximate a solvent-specimen interface, wherein the plug volume region is in fluid communication with the probe 12; and draining the plug volume through the sampling capillary 20. The chemical composition of the drained plug volume 60 can be analyzed with an analytical instrument 32.

Figure 8:
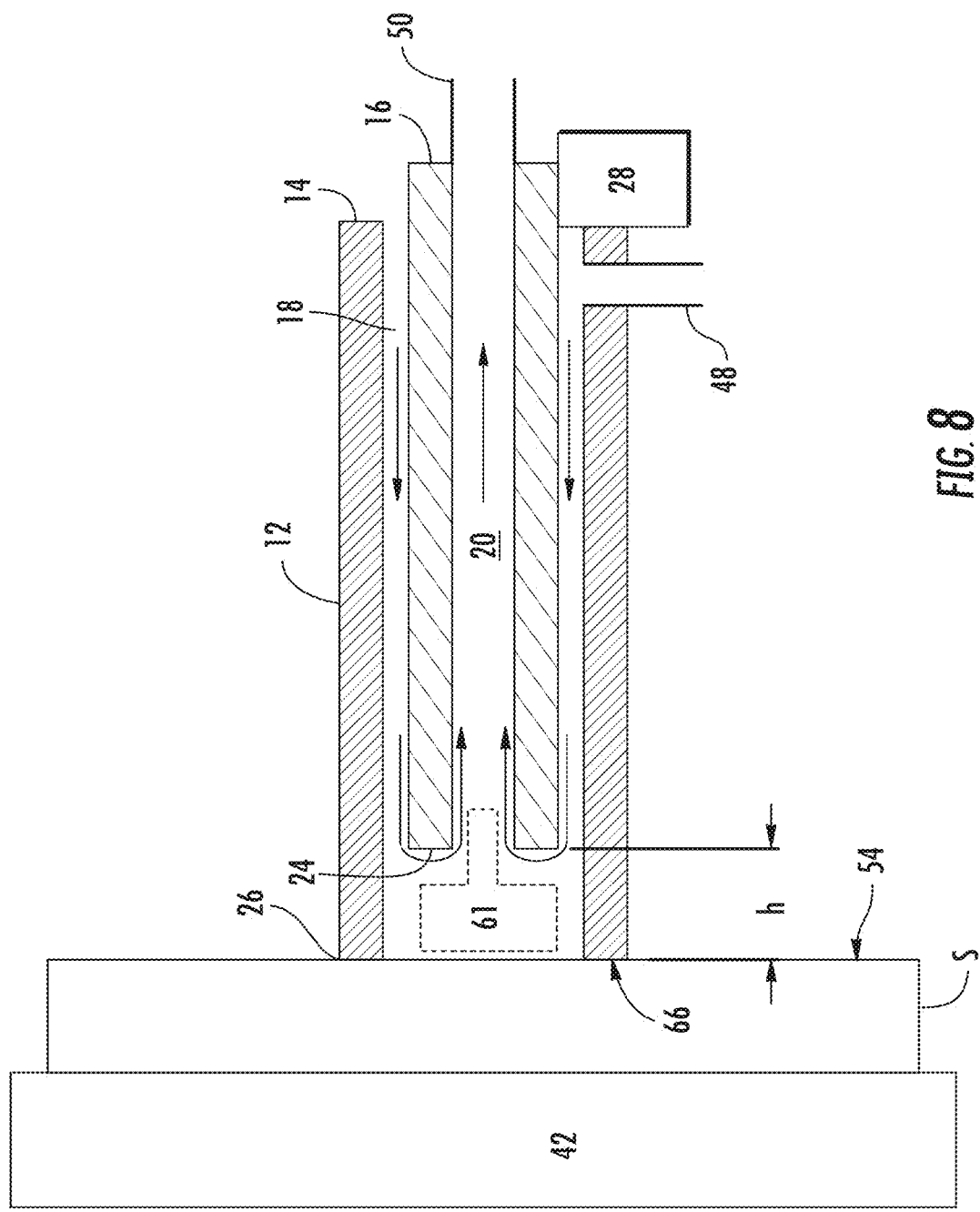
FIG. 8 is a cross-section of the probe shown in FIG. 1 taken along cut line A-A' where the capillary ratio is less than the plug ratio threshold and the junction is a contact junction.

The contacting step can include comprises forming a junction between a distal end 22 of the probe 12 and a surface 54 of the target site 44. As used herein, the term "junction" can refer to a contact junction 66, as shown in FIGS. 7 & 8, or a liquid junction 62, such as shown in FIGS. 2-4.

The specimen (S) can include a plurality of target sites 44, and the method can include repeating the contacting, maintaining, draining and analyzing steps for each of the plurality of target sites 44. Concurrent with or following the analyzing step for a given target site 44, the probe 12 can be repositioned so that the solvent 19 is in contact with the next target site 44. Although the junction 62 and/or 66 between the probe 12 and the surface 54 can be broken during the repositioning step, in some examples the junction 62 and/or 66 between the probe 12 and the surface 54 can be maintained during the repositioning step. As will be understood, where the target site 44 is a sampling line 56, the junction 62 and/or 66 will be maintained while the probe is moved along the entire sampling line 56.

In examples where the junction 62 and/or 66 is not broken, a separate plug volume 60 can be formed for each target site 44. For example, a plug volume 60 may be formed over a first target site 44 by retracting the inner capillary tip 24 and increasing inter-tip distance (h) until it exceeds the plug ratio threshold. The analyte obtained from the first target site 44 may then be analyzed by reducing the inter-tip distance (h) below the plug ratio threshold in order to drain the plug sampling liquid 61 through the sampling capillary 20 to the analytical instrument 32. The probe 12 can then be repositioned over a second target site 44 and the inter-tip distance (h) can be increased until it exceeds the plug ratio threshold and another plug volume 60 formed. This process can be repeated until all target sites 44 along the sampling path 52 have been analyzed via analysis of a separate plug volume 60. Similarly, the plug volume 60 can be formed and drained by changing the flow rates of the sampling outlet 50 and solvent inlet 48 as described herein.

In examples where the junction 62 and/or 66 is broken, a plug volume 60 can be formed for each target site 44. For example, a plug volume 60 can be formed over a first target site 44 by retracting the inner capillary tip 24 and increasing inter-tip distance (h) until it exceeds the plug ratio threshold. The analyte obtained from the first target site 44 may then be analyzed by reducing the inter-tip distance (h) below the plug ratio threshold in order to drain the plug sampling liquid 61 through the sampling capillary 20 to the analytical instrument 32. The junction 62 and/or 66 can be broken and the probe 12 can then be repositioned over a second target site 44 and the inter-tip distance (h) can be increased until it exceeds the plug ratio threshold. A junction 62 and/or 66 can be formed either before or after the inter-tip distance (H) is adjusted to form the plug volume 60. This process can be repeated until all target sites 44 along the sampling path 52 have been analyzed. Similarly, the plug volume 60 can be formed and drained by changing the flow rates of the sampling outlet 50 and solvent inlet 48 as described herein or by breaking the junction 62.

Although breaking an existing junction 62 and/or 66 can cause a plug volume 60 to drain, it has been determined that this only occurs in very specific circumstances. Generally, the capillary ratio (h/H) must approximate the plug ratio threshold in order for breaking an existing junction 62 and/or 66 to cause a plug volume to drain. In instances where the capillary ratio is less than the plug ratio threshold, there is no plug volume 60 to drain, whereas when the capillary ratio exceeds the plug ratio threshold by a significant amount, the plug volume 60 can be maintained in the absence of the junction 62 and/or 66. Thus, in order for breaking the junction 62 and/or 66 to cause the plug volume 60 to drain, the capillary ratio should be no more than 15% above the plug ratio threshold, or no more than 10% above the plug ratio threshold.

The solvent 18 can include a reactant selected to react with a target analyte. For example, in some instances a reaction product of an analyte may be easier to distinguish from contaminants that may also be present at the target site 44. In such instances, it may be beneficial to include a reactant or catalyst in the solvent.

An alternative to including a reactant or catalyst in the solvent 18 is the use of reactant spots 68 that include a desired reactant or catalyst and are deposited adjacent to one or more target sites 44, as shown in FIG. 6. In such instances, the probe 12 may be positioned to contact the solvent 19 with the target site 44 and then subsequently with a reactant spot 68 in order to facilitate a reaction. The plug volume 60 can be maintained while the solvent 19 is contacted with the target site 44 and the reactant spot 68 either simultaneously or sequentially. The order of contacting is not generally of importance, so the solvent 19 can be contacted with the target site 44 then the reactant spot 68 or vice versa.

Once the plug volume 60 is formed, the contact time between the solvent 19 and the target site 44 and/or the reactant spot 68 can be, independently, at least 5 seconds, at least 10 seconds, at least 15 seconds, at least 20 seconds, at least 30 seconds, or at least 45 seconds. For example, the plug volume 60 formed and the solvent 19 can be contacted with the target site 44 for 30 seconds and subsequently with the reactant spot 68 for 10 seconds. Of course, the probe may be moved continuously over a sequence of target sites and reactant spots causing the contact time to be less than 5 seconds. Although the reactant spot 68 may be present, in many instances, no reactant spot will be present.

EXAMPLES

Figure 9A:
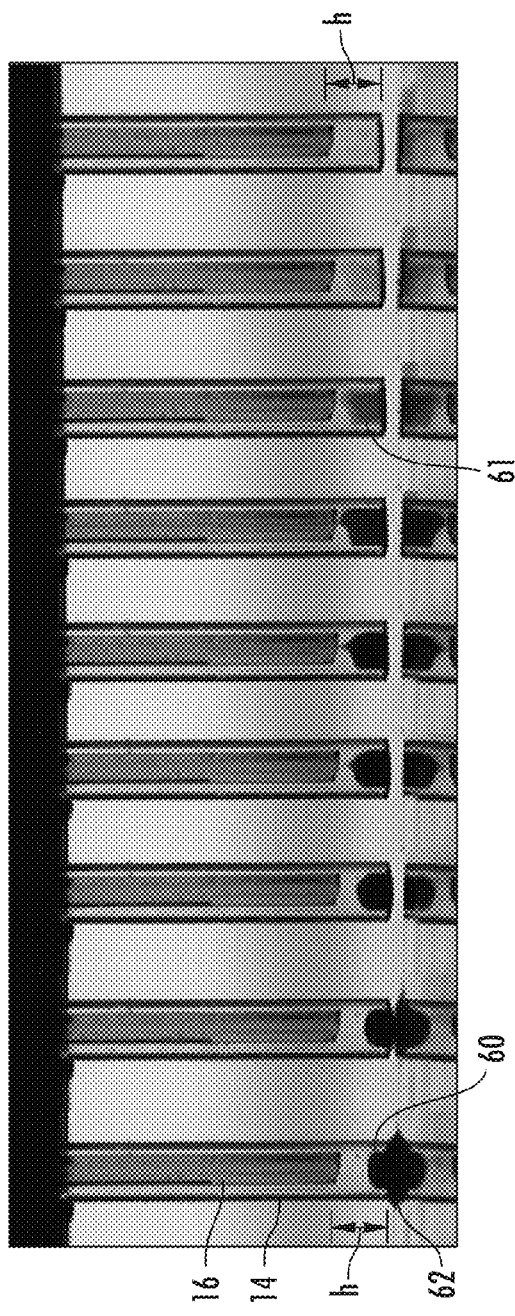
FIGS. 9A and B are time lapse sequences showing the formation a plug volume and the draining of the plug sampling liquid.

FIG. 9A shows a time lapse sequence (left to right) of sampling conducted using a dual-capillary probe 12 having inner and outer capillary tubes 16, 14. In the probe 12 used in the examples, the outer diameter and inner diameter of the outer capillary are ~950 µm and ~450 µm, respectively, while the outer diameter and inner diameter of the inner capillary are ~360 µm and ~120 µm, respectively. In these embodiments, the plug volume 60 is formed where the inner capillary 16 is recessed h=400 µm within the outer capillary 14, while draining of the plug sampling liquid 61 occurs due to the junction breakage with a capillary ratio sufficiently near to the plug ratio threshold, e.g., 0.9 in this case.

In the time lapse sequence, a plug volume 60 is formed and the plug sampling liquid 61 is subsequently drained. Starting at the far left a liquid micro-junction is formed over a target site that includes a visible analyte. As can be seen, a well-defined plug volume 60 forms immediately above the surface of the specimen. In the third image from the left, the junction 62 has just broken from the surface 54. This image was captured before the induced jet of plug sampling liquid 61 in the fourth image from the left was visibly entrained into the sampling capillary 20. In the fourth, fifth and sixth images from the left, this plume can be seen flowing in to the inner capillary tube 16, i.e., the sampling capillary 20. In the three images closest to the right, the plug sampling volume 61 becomes less distinct and eventually disappears. This sequence demonstrates the formation and draining of the plug volume.

Figure 9B:
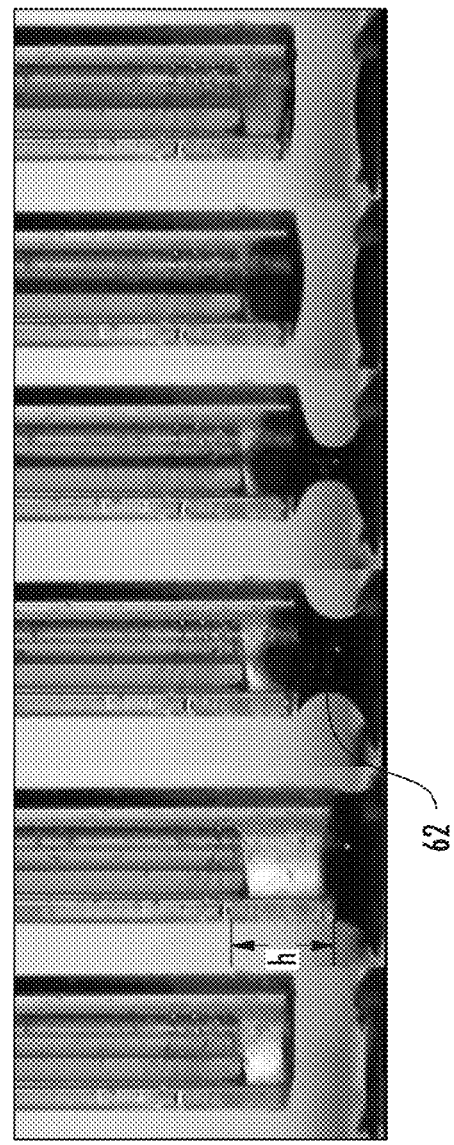

FIG. 9B is a close-up time lapse sequence similar to that in FIG. 9A. In this sequence, the outer capillary tube 14 is extended toward the surface until a liquid micro-junction 62 is formed. At that point, as shown in the second image from the left, the visible analyte dissolved into the liquid micro-junction region. The third and fourth images from the left show the outer capillary tube 14 being retracted until the liquid micro-junction breaks. The three images closed to the right, show that the plug sampling liquid 61 is then drained by the inner capillary tube 16, i.e., the sampling capillary 20.

FIG. 10 shows a time lapse sequence where the probe is dragged from a target site 44 to a reactant spot 68 while the plug volume 60 and a liquid micro-junction 62 are maintained. FIG. 10A shows an initial image with a droplet of solvent 19 extending from the probe 12 above the target site 44. FIG. 10B shows a liquid micro-junction 62 has formed between the probe 12 and the target site 44 and a plug volume 60 has formed in the micro-junction region, which includes a light colored analyte. FIGS. 10C and D show the liquid micro-junction after the probe 12 is moved over a reactant spot 68, which includes a darker colored reactant. In FIGS. 10E and F, the inter-tip distance (h) is reduced by retracting the outer capillary tube 14 until the liquid micro-junction 60 breaks. FIGS. 10F-H show the plug sampling liquid being drained through the inner capillary tube 14, i.e., the sampling capillary 20.

While the invention has been described in terms of specific embodiments, it is evident in view of the foregoing description that numerous alternatives, modifications and variations will be apparent to those skilled in the art. Accordingly, the invention is intended to encompass all such alternatives, modifications and variations which fall within the scope and spirit of the invention and the following claims.

What is claimed is:

1. A system comprising for analyzing a chemical composition of a specimen comprising:
   a probe comprising:
   an outer capillary tube, and
   an inner capillary tube disposed co-axially within said outer capillary tube, said inner and outer capillary tubes defining a solvent capillary and a sampling capillary in fluid communication with one another at a distal end of the probe;
   the outer capillary tube having an inner diameter H, and h is a distance between a tip of said outer capillary and a tip of said inner capillary tube, solvent flowing through the solvent capillary forming a continuous liquid microjunction across the surface of the specimen spanning at least the inner diameter H of the outer capillary tube;
   an adjuster coupled to said outer capillary tube and said inner capillary tube, said adjuster for moving a tip of said outer capillary tube and a tip of said inner capillary tube longitudinally relative to one another; and
   a controller communicatively coupled to said adjuster, said controller being configured for actuating said adjuster to impart relative longitudinal motion between said outer capillary tube and said inner capillary tube, wherein the controller actuates said adjuster to maintain a plug volume proximate a solvent-specimen interface and within the liquid microjunction, the plug volume having a height less than h, wherein said plug volume is in fluid communication with said probe and the capillary ratio (h/H) exceeds 1.0.

2. The system according to claim 1, further comprising:
   an analytical instrument for determining a chemical composition of an analyte, wherein a sampling capillary is in fluid communication with said analytical instrument.

3. The system according to claim 2, wherein said analytical instrument is a mass spectrometer, an ionization source, a spectroscopy method; a separation method, or a combination thereof.

4. The system according to claim 2, further comprising:
   a specimen stage; and
   a stepper mechanism configured to provide relative motion between said specimen stage and said probe.

5. The system according to claim 4, wherein said stepper mechanism is communicatively coupled to said controller, said controller being configured for actuating said stepper to sequentially articulate said probe and said specimen stage along a predetermined sampling path comprising a plurality of target sites.

6. The system according to claim 4, wherein a chemical composition of an analyte desorbed at each of said plurality of target sites is determined by said analytical instrument and a plot of said data is generated.

7. The system according to claim 1, wherein the capillary ratio is at least 1.5.

8. The system according to claim 1, wherein the capillary ratio is at least 1.75.

9. The system according to claim 1, wherein the capillary ratio is at least 2.0.

10. The system according to claim 1, wherein the capillary ratio is from 1.0 to 2.0.

* * * * *